United States Patent [19]
Rubin et al.

[11] Patent Number: 6,156,771
[45] Date of Patent: Dec. 5, 2000

[54] METHOD FOR ALLEVIATION OF LOWER GASTROINTESTINAL DISORDERS IN A HUMAN PATIENT

[76] Inventors: Walter Rubin, 1708 Riverview Rd., Gladwyne, Pa. 19035; Bhavin Dave, 262 Pine Valley Dr., Dover, Del. 19904

[21] Appl. No.: 09/082,699

[22] Filed: May 21, 1998

Related U.S. Application Data

[60] Provisional application No. 60/058,013, Aug. 28, 1997.

[51] Int. Cl.⁷ .................................................. A61K 31/445
[52] U.S. Cl. ............................................................. 514/330
[58] Field of Search ............................................. 514/330

[56] References Cited

U.S. PATENT DOCUMENTS

| | | | |
|---|---|---|---|
| 5,330,982 | 7/1994 | Tyers | 514/214 |
| 5,403,830 | 4/1995 | Place | 514/184 |
| 5,705,190 | 1/1998 | Broad et al. | 424/465 |

OTHER PUBLICATIONS

Dickinson, 1994, J. Clin. Gastroenterol 18:317–319.
Heinzow and Schlegelberger, Feb. 1994, The Lancet 343:477.
Manrique et al., 1993, Rev. Clin. Esp. 193:378–379.
Roblin et al., 1991, Ann. DeGastroenterologie et D'Ang. 27:177–178.
Aggarwal et al., 1994, Gastroenterology 106:945–950.
Drossman et al., 1997, Gastroenterology 112:2120–2137.
Drossman et al., 1994, Appendix A, Diagnostic Criteria for Functional Gastrointestinal Disorders, Degnon and Associates, McLean, VA.
Evans et al., 1996, Gastroenterology 110:393–404.
Gorard et al., 1994, Gut 35:203–210.
Hasler et al., American Gastroenterological Association, 1997, Gastroenterol. 112:2118–2119.
Hasler et al., 1995, In: *Textbook of Gastroenterology*, 2nd ed., Yamada, Ed., J.B. Lippincott Co., Philadelphia, pp. 1832–1855 Chapter 81.
Hyams, 1983, Gastroenterology 84:30–33.
Jacobsen et al., 1986, Scand. J. Gastroenterol. 21:824–828.
Kellow et al., 1990, Gastroenterology 98:1208–1218.
Klein, 1988 Gastroenterology 95:232–241.
Lindstrom, 1976, Pathol. Europ. 11:87–89.
Locke, Gastroenterology Clinics of North America Mar. 1996; 25:1–19.
Manning et al., 1978, Br. Med. J. 2:653–654.
Maxson et al., Nov. 1994, Med. Clin. N. Am. 78:1259–1273.
Merrick et al., Mar. 1985, Br. Med. J. 290:665–668.
Nanda et al., 1989, Gut 30:1099–1104.
Nelis et al.; 1990, Gastroenterology 98:A194.
O'Brien et al., Mar. 1996, Gastroenterol. Clin. N. Am. 25:147–162.
Oddson et al., 1978, Scand. J. Gastroenterol. 13:409–416.
Owyang et al., 1995, In: *Textbook of Gastroenterology*, 2nd ed., Yamada, Ed., J. B. Lippincott Co., Philadelphia, pp. 2091–2112.
Read et al., 1980, Gastroenterology 78:264–271.
Rogler et al., 1996, Dtsch. Med. Wschr. 121:1531–1536.
Rumessen et al., 1988, Gastroenterology 95:694–700.
Schiller et al., 1987, Gastroenterology 92:151–160.
Schmidt et al., 1996, Scand. J. Gastroenterol. 31:581–589.
Sjölund et al., 1987, Scand. J. Gastroenterol. 130(Suppl):15–19.
Talley et al., Oct. 1991, Gastroenterology 101:927–934.
Taylor et al., 1980, Gut 21:843–847.
Thaysen et al., 1976, Gut 17:965–970.
Thompson et al., 1989, Gastroenterol. Intl. 2:92–95.
Thompson et al., 1992, Gastroenterol. Intl. 5:75–91.
Weser et al., Nov. 1965, N. Eng. J. Med. 273: 1070–1075.
Weser et al., 1979, Gastroenterology 77: 572–579.
Whitehead, Mar. 1996, Gastroenterol. Clin. N. Am. 25:21–34.
Wiley et al., 1988, Gastroenterology 94:1144–1149.
Murthy et al. 1997, Exp. Opin. Ther. Patents 7:1–21.

*Primary Examiner*—Kathleen K. Fonda
*Attorney, Agent, or Firm*—Akin, Gump, Strauss, Hauer & Feld, L.L.P.

[57] ABSTRACT

A method of alleviating a lower GI symptom in a human patient afflicted with a lower GI disorder and a method of treating a human patient afflicted with a lower GI disorder, including, for example, a patient afflicted with irritable bowel syndrome or a patient afflicted with functional diarrhea, are provided. Each of these methods comprises inhibiting gastric secretion by the patient, such as by administering to the patient a pharmaceutical preparation comprising an effective amount of an inhibitor of gastric secretion.

19 Claims, No Drawings

METHOD FOR ALLEVIATION OF LOWER GASTROINTESTINAL DISORDERS IN A HUMAN PATIENT

CROSS REFERENCE TO RELATED APPLICATIONS

This application is entitled to priority pursuant to 35 U.S.C. §119(e) to U.S. provisional patent application 60/058,013, filed on Aug. 28, 1997.

FIELD OF THE INVENTION

The field of the invention is alleviation of lower gastrointestinal (GI) disorders in a human patient and alleviation of lower GI symptoms associated with such disorders.

BACKGROUND OF THE INVENTION

Between about 5% and about 10% of the U.S. population suffers from chronic diarrhea for which an organic cause cannot be identified (Camilleri et al., 1977, Aliment Pharmacol Ther. 11:3–15; Talley et al., 1991, Gastroenterology 101:927–934). The diarrhea may be persistent or may alternate with periods of normal bowel habit or with periods of constipation. Chronic diarrhea which is not accompanied by abdominal. pain and which is not attributable to an organic cause is referred to as "functional diarrhea" (FD) or "chronic idiopathic diarrhea" (Drossman et al., 1997, Gastroenterology 112:2120–2137; Hasler et al., 1995, In: *Textbook of Gastroenterology*, 2nd ed., Yamada, Ed., J. B. Lippincott Co., Philadelphia, pp. 1832–1855; Camilleri et al., supra; Drossman et al., 1994, *The functional Gastrointestinal disorders: Diagnosis, Pathophysiology, and Treatment*, Degnon and Associates, McLean, Va.; Thompson et al., 1992, Gastroenterol. Intl. 5:75–91). Chronic diarrhea which is associated with abdominal pain and which is not attributable to an organic cause is referred to as "irritable bowel syndrome with a diarrhea predominance" (IBS; Hasler et al., supra; American Gastroenterological Association, 1997, Gastroenterol. 112:2118–2119; Drossman et al., 1997, Gastroenterol. 112:2120–2137; Camilleri et al., supra).

Postprandial urgency or postprandial accentuation of lower GI symptoms are common manifestations of both IBS and FD. Patients afflicted with either IBS or FD frequently experience an urgency to defecate after eating, and sometimes attribute this urgency to the ingestion of particular foods other than lactose. Furthermore, some of these patients associate exacerbation of their symptoms with emotional stress. These symptoms have led investigators of IBS and FD to believe that abnormal physiological factors, psychological factors, or both, may be associated with IBS and FD (Drossman et al., supra; Hasler et al., supra; Camilleri et al., supra; Drossman et al., supra; Drossman et al., supra; O'Brien et al., 1996, Gastroenterol. Clin. N. Am. 25:147–162; Bazzocchi et al., 1991, Gastroenterology 101:1298–1306; Choi et al., 1997, Am. J. Gastroenterol. 92:297–306; Aggarwal et al., 1994, Gastroenterology 106:945–950; Quigley, 1996, Gastroenterol. Clin. N. Am. 25:113–145; Schmidt et al., 1996, Scand. J. Gastroenterol. 31:581–589; Evans et al., 1996, Gastroenterology 110:393–404; Gorard et al., 1994, Gut 35:203; Kellow et al., 1990, Gastroenterology 98:1208; Whitehead, 1996, Gastroenterol. Clin. N. Am. 25:21–34). No effective therapy has been established for the chronic diarrhea or the postprandial urgency associated with either IBS or FD (Drossman et al., 1997, supra; Hasler et al., supra; Camilleri et al., supra; Drossman et al., 1994, supra; Thompson et al., supra; Klein, 1988 Gastroenterology 95:232–241).

IBS is believed to be a heterogeneous group of disorders, characterized by chronic lower gastrointestinal symptoms not associated with an identifiable organic cause. IBS is one of the most common chronic afflictions, not only in the U.S., but also in many other countries where it has been studied. It has been estimated that approximately between 9% and 22% of the U.S. population is afflicted with IBS. Most people afflicted with IBS, probably over 70% of such people, do not seek a physician's care. Nonetheless, people afflicted with IBS miss about 3 times as many work days as people not so afflicted. Furthermore, IBS sufferers account for about 12% of primary care practice and about 28% of gastroenterological practice, and constitute nearly half of the outpatients who are referred to gastroenterologists.

The "spastic" variety of IBS, which is characterized by abdominal pain and constipation, is believed to be somewhat more common than IBS associated with chronic diarrhea and postprandial urgency. However, as noted above, the "diarrhea predominance" variety is also common. Because the definition and diagnosis of IBS have been somewhat controversial, attempts have been made in recent years to reach some consensus regarding the definition of IBS and other functional or non-organic GI disorders, and the clinical criteria for their diagnosis (Drossman et al., supra; Hasler et al., supra; Camilleri et al., supra; Drossman et al., supra; Thompson et al., 1989, Gastroenterol. Intl. 2:92–95; Manning et al., 1978, Br. Med. J. 2:653–654 and Thompson et al., supra). According to the so-called "Rome criteria," patients afflicted with chronic diarrhea not attributable to an organic cause and not accompanied by significant abdominal pain are classified as having FD, and those patients afflicted with chronic diarrhea not attributable to an organic cause and accompanied by significant abdominal discomfort are classified as having IBS with diarrhea predominance (Drossman et al., supra; Hasler et al.,supra; Camilleri et al., supra; Drossman et al., supra; Thompson et al., supra; Manning et al., supra).

Several possible etiologies and pathophysiological mechanisms have been suggested for IBS and FD, including a psychophysiological or psychosomatic mechanism, a primary motor or dysmotility mechanism such as an exaggerated gastrocolic reflex due to some neural, endocrine, or muscle dysfuinction, or some combination thereof, and a visceral hypersensitivity mechanism (Drossman et al., 1997, supra; Hasler et al., supra; Camilleri et al., supra; Drossman et al., 1994, supra; O'Brien et al., supra; Bazzocchi et al., supra; Choi et al., supra; Aggarwal et al., supra; Quigley, et al., supra; Schmidt et al., supra; Evans et al., supra; Gorard et al., supra; Kellow et al., supra; Whitehead et al., supra; Suolund et al., 1987, Scand. J. Gastroenterol. 130(Suppl) :15–20). Furthermore, certain patients previously thought to have IBS have been discovered to have identifiable GI disorders, such as lactase deficiency, collagenous colitis, and lymphocytic (microscopic) colitis (Weser et al., 1965, N. Eng. J. Med. 273: 1070–1075; Maxson et al., 1994, Med. Clin. N. Am. 78: 1259–1273; Lindstrom, 1976, Pathol. Err. 11:87–89 and Read et al., 1980, Gastroenterology 78:264–271). Today, before a diagnosis of IBS or FD is made, these "organic" causes of chronic diarrhea should be excluded.

It has been suggested that some IBS or FD patients actually have cholereic diarrhea due to a colonic or small intestinal hypersensitivity to bile acids or an inapparent malabsorption of bile acids (Drossman et al., 1997, Gastroenterology 112:2120–2137; Hasler et al., 1995, In: *Textbook of Gastroenterology*, 2 nd ed., Yamada, Ed., J. B. Lippincott Co., Philadelphia, pp. 1832–1855; Camilleri et al., supra;

Drossman et al., 1994, *The functional Gastrointestinal disorders: Diagnosis, Pathophysiology, and Treatment*, Degnon and Associates, McLean, Va.; Taylor et al., 1980, Gut 21:853; Oddson et al., 1978, Scand. J. Gastroenterol. 13:409–416; Thaysen et al., 1976, Gut 17:965–970; Merrick et al., 1985, Br. Med. J. 290:665–668; Schiller et al., 1987, Gastroenterology 92:151–160). However, an apparent response to administration of cholestyramine, which is a constipating agent that was administered to IBS patients in certain of these studies, should not necessarily establish the presence of such a disorder. In addition, the role that dietary sorbitol, fructose, and food allergens may have in the development of lower GI symptoms in some patients remains unclear (Camilleri et al., supra; Nanda et al., 1989, Gut 30:1099–1104; Hyams, 1983, Gastroenterology 84:30–33; Rumessen et al., 1988, Gastroenterology 95:694–700; Nelis et al., 1990, Gastroenterology 98:A194).

Collagenous colitis is a condition characterized by chronic diarrhea and abnormalities of the colonic mucosa. Colonoscopy of patients afflicted with collagenous colitis usually reveals no apparent abnormality. However, biopsies of the colonic mucosa of such patients, which are usually obtained at the time of colonoscopy or sigmoidoscopy reveals inflammation of colon tissue and the presence of an abnormal collagen layer below the surface epithelium.

Ulcerative colitis is an inflammatory disease of the colon characterized by chronic diarrhea which is often bloody. Ulcerative colitis may affect only a portion of the colon or it may affect the entire length of the colon, in which case the disease is designated 'pan-ulcerative colitis.'

Giardiasis is an example of an infectious disease characterized by diarrhea, which is often chronic and which is caused by a parasite (the protozoan *Giardia lamblia*). Other parasites and infectious agents, such as bacteria and viruses, cause diarrhea which may be acute or chronic.

Many previous treatments for chronic diarrhea in patients afflicted with IBS or FD have proven to have limited, if any, efficacy. These previous treatments include restrictive diets, administration of fiber, loperamide, diphenoxylate, other opiates, anticholinergics, antispasmodics, cholestyramine, tricylic and serotonin reuptake inhibitor antidepressants, sedatives, and psychological therapy. Patients afflicted with IBS and FD have been treated with limited success by administering anticholinergic agents to reduce intestinal motility in those patients. It was presumed that these anticholinergic agents achieved their effect by inhibiting stimulant cholinergic innervation pathways of the intestines, and not owing to any capacity of such agents to inhibit gastric secretion.

Clearly, therefore, a significant unmet need remains for an efficacious treatment of patients afflicted with lower GI disorders, including alleviation of lower GI symptoms, such as chronic diarrhea and postprandial urgency, which are associated with lower GI disorders such as IBS or FD.

SUMMARY OF THE INVENTION

The invention relates to a method of alleviating a lower GI disorder in a human patient. This method comprises suppressing gastric secretion by the patient.

In one embodiment of this method, gastric secretion is suppressed by administering to the human patient a pharmaceutical composition comprising an effective amount of an inhibitor of gastric secretion.

In still another aspect of this method, the inhibitor of gastric secretion is selected from the group consisting of a proton pump inhibitor, a histamine $H_2$-receptor blocker, omeprazole, lansoprazole, cimetidine, ranitidine, nizatidine, and famotidine. For example, the administering step may comprise administering about 30 milligrams of lansoprazole per day, about 20 milligrams of omeprazole per day, about 20 milligrams of famotidine twice per day, or about 150 milligrams of ranitidine twice per day.

In yet another aspect of this method, the pharmaceutical composition further comprises a symptomatic anti-diarrheal agent, such as one selected from the group consisting of loperamide, hyoscyamine, atropine, furazolidone, loperamide, diphenoxylate, difenoxin, bismuth subsalicylate, and octreotide.

In another embodiment of this method, the lower GI disorder is one, such as IBS or FD, that is not attributable to an organic cause.

In another aspect, the lower GI disorder is one which has an identifiable organic cause, such as a lower GI disorder selected from the group consisting of ulcerative colitis, collagenous colitis, microscopic colitis, lymphocytic colitis, inflammatory bowel disease, Crohn's disease, and an infectious diarrhea such a diarrhea caused by amebiasis, giardiasis, a viral infection, cytomegalovirus infection, or a pathogenic bacterial infection. The pathogenic bacterial infection may, for example, be selected from the group consisting of an infection by a bacterium of the genus Escherichia, an *Escherichia coli* 0157:H7 infection, an infection by a bacterium of the genus Salmonella, an infection by a bacterium of the genus Campylobacter, an infection by a bacterium of the genus Shigella, and an infection by a bacterium of the genus Yersinia.

In still another embodiment of this method, the lower GI disorder is characterized by a lower GI symptom selected from the group consisting of diarrhea, chronic diarrhea, acute diarrhea, abdominal pain associated with diarrhea, postprandial urgency, postprandial accentuation of diarrhea, postprandial accentuation of abdominal pain, and a combination of these symptoms. Preferably, the lower GI symptom is chronic diarrhea and postprandial urgency or accentuation of diarrhea.

The invention also relates to a kit comprising an inhibitor of gastric secretion and an instructional material which describes administering the inhibitor to a human patient afflicted with a lower GI disorder for alleviation of a lower GI symptom in the patient or for alleviation of the lower GI disorder.

In one embodiment of this kit, the inhibitor of gastric secretion is selected from the group consisting of a proton pump inhibitor, a histamine $H_2$-receptor blocker, omeprazole, lansoprazole, cimetidine, ranitidine, nizatidine, and famotidine.

In another embodiment of this kit, the inhibitor is a unit dosage form of the inhibitor, such as a unit dosage form comprising about 30 milligrams of lansoprazole, a unit dosage form comprising about 20 milligrams of omeprazole, a unit dosage form comprising about 20 milligrams of famotidine, and a unit dosage form comprising about 150 milligrams of ranitidine.

The invention further relates to a method of alleviating a lower GI symptom in a patient afflicted with a lower GI disorder. This method comprises suppressing gastric secretion by the patient. In one embodiment of this method, gastric secretion is suppressed by administering to the patient a pharmaceutical composition comprising an effective amount of an inhibitor of gastric secretion.

DETAILED DESCRIPTION

The invention relates to methods and kits for alleviating human lower GI disorders and for alleviating symptoms associated with such disorders.

It has been discovered in the present invention that suppression of gastric secretion alleviated chronic diarrhea (CD), postprandial urgency, and cramps, if present, in all twenty-five of twenty-five patients studied in two groups, each of whom was afflicted with either FD or IBS. Five of the twenty-five patients were afflicted with IBS or FD and postprandial urgency and gastroesophageal reflux disease (GERD), and were administered an inhibitor of gastric secretion for the purpose of alleviating GERD symptoms. Surprisingly, CD and postprandial urgency, as well as the GERD symptoms, were relieved in all five of these patients. Subsequent to this observation, various inhibitors of gastric secretion were used in a prospective therapeutic study of twenty patients afflicted with IBS or FD who experienced symptoms including chronic diarrhea with postprandial urgency or accentuation of symptoms. All twenty of the patients in this therapeutic trial obtained rapid relief from their CD, postprandial urgency, and cramps, if present, these symptoms usually abating within three days. Inhibitors of gastric secretion therefore provide a new, efficacious, and well tolerated therapy for chronic diarrhea, postprandial urgency, and cramps, if any, of patients afflicted with FD or IBS.

It has furthermore been discovered in the present invention that suppression of gastric secretion alleviated lower GI symptoms, such as diarrhea, pain, and postprandial urgency, which are associated with lower GI disorders having known organic causes. For example, anti-secretory therapy, as described herein, relieved diarrhea, postprandial urgency, and cramps, if present, in some patients afflicted with ulcerative colitis, collagenous colitis, giardiasis, and pathogenic bacterial infections.

Numerous methods of suppressing gastric secretion are known in the art. They have been used to treat or prevent acid-related upper GI disorders such as peptic ulcer, GERD, and gastritis. However, none of these methods has previously been known to be effective to alleviate a lower GI disorder or to alleviate a lower GI symptom such as diarrhea or postprandial urgency, except as noted herein. Known methods of suppressing gastric secretion in a human patient include administration to the patient of an inhibitor of gastric secretion, surgical resection of a portion of the patient's stomach, and severance of the patient's vagus nerves. Administration to a patient of an inhibitor of gastric secretion is a preferred method of suppressing gastric secretion in the patient.

It is understood that inhibitors of gastric secretion have been used previously to treat diarrhea symptoms in patients afflicted with particular organic disorders known to be associated with excessive gastric secretion. For example, administration of an inhibitor of gastric secretion effectively controls the diarrhea that occurs in about 40% of patients afflicted with Zollinger-Ellison syndrome. It has been thought that inhibitors of gastric secretion alleviate Zollinger-Ellison-associated diarrhea by reducing the large volume of hypersecreted gastric juice that these patients produce. It has been presumed that hypersecretion of gastric juice introduces into the proximal small intestine of a patient afflicted with Zollinger-Ellison syndrome more fluid than can be adequately absorbed by the small and large intestine. The hypersecretion also leads to excessive acidity in the proximal small intestine and thus to malabsorption due probably to denaturation of pancreatic lipase and perhaps the impairment of intestinal micelle formation or damage to intestinal mucosa (DelValle et al., 1995, In: *Textbook of Gastroenterology*, 2nd ed., Yamada, Ed., J. B. Lippincott Co., Philadelphia, pp. 1430–1445).

Antisecretory agents have also been effectively used to treat some patients afflicted with the short-bowel syndrome who, like patients afflicted with Zollinger-Ellison syndrome, commonly experience gastric hypersecretion. Gastric hypersecretion is especially pronounced soon after extensive small-intestinal resection procedures, and is thought to contribute to diarrhea and malabsorption experienced by resected patients (Weser et al., 1979, Gastroenterology 77:572–579; Cortot et al., 1979, N. Engl. J. Med. 300:79–80; Aly et al., 1980, Acta Med. Scand. 207:119–122; Jacobsen et al., 1986, Scand. J. Gastroenterol. 21:824–828).

Inhibitors of gastric secretion have also been used successfully to treat patients who have diarrhea and malabsorption due to pancreatic insufficiency and who fail to respond optimally to pancreatic digestive enzymes alone (Owyang et al., 1995, In: *Textbook of Gastroenterology*, 2nd ed., Yamada, Ed., J. B. Lippincott Co., Philadelphia, pp. 2091–2112). Presumably, gastric secretion inhibitors protect the lipase tablets administered to such patients by reducing inactivation of lipase caused by the patient's gastric acid.

IBS and FD patients have previously been treated with limited success with anticholinergic agents in order to reduce intestinal motility and the gastrocolic response. It has been presumed that these agents mediated their effects by inhibiting stimulatory cholinergic innervation of the intestines, not because of the modest gastric-secretion-inhibitory activity that such agents have (Drossman et al., 1997, Gastroenterology 112:2120–2137; Hasler et al., 1995, In: *Textbook of Gastroenterology*, 2nd ed., Yamada, Ed., J. B. Lippincott Co., Philadelphia, pp. 1832–1855; Camilleri et al., supra; Drossman et al., 1994, *The functional Gastrointestinal disorders: Diagnosis, Pathophysiology, and Treatment*, Degnon and Associates, McLean, Va.; Klein, 1988, Gastroenterology 95:232–241; Wiley et al., 1988, Gastroenterology 94:1144–1149).

Proton pump inhibitors have been used with some success to treat diarrhea in rare patients afflicted with congenital chloridorrhea (Aichbichler et al., 1997, N. Eng. J. Med. 336:106–109). These patients exhibit intestinal malabsorption of chloride. Suppression of normal secretion of HCl in the stomachs of these patients reduces the chloride load to the intestine, and their diarrhea is thereby somewhat improved.

Omeprazole has been reported to benefit two patients afflicted with collagenous colitis (Roblin et al., 1991, Ann. Gastroenterol. Hepatol. 27:177–178; Manrique et al., 1993, Rev. Clin. Esp. 193:378–379). However, in those studies, it was presumed that omeprazole mediated its beneficial effects by some unknown mechanism that specifically reverses the pathology of collagenous colitis. Hence, the importance of inhibiting gastric secretion was not recognized in those studies.

No one has previously taught or suggested that inhibition of gastric secretion may be used to alleviate lower GI symptoms, such as diarrhea, pain, or postprandial symptoms such as postprandial urgency, in patients afflicted with a lower GI disorder such as IBS or FD. No one has taught or suggested that inhibition of gastric secretion is effective to alleviate lower GI disorders or symptoms not known to be associated with excessive gastric secretion. The only exceptions to this statement relate to the administration of inhibitors of gastric secretion in conjunction with lipase medications for the purpose of preserving or extending lipase activity in patients afflicted with pancreatic insufficiency and administration of inhibitors of gastric secretion for the purpose of reducing intestinal chloride load in the rare patient afflicted with congenital chloridorrhea. The observations herein that therapy to suppress gastric secretion is useful for alleviating lower GI disorders and symptoms are therefore surprising.

Given the prevalence of lower GI disorders and their associated symptoms in the population, and further given the critical unmet need for an efficacious treatment for such disorders and their associated symptoms, a treatment capable of alleviating such disorders or symptoms as efficacious as that described herein would have been widely heralded and rapidly adopted within the gastroenterology community. This has not occurred. The efficacy of the treatment described herein, coupled with the fact that there has been no report or suggestion of the use of a gastric secretion inhibitor to alleviate these disorders and symptoms, provides overwhelming evidence of the surprising nature of the present invention.

One skilled in the art upon reading the present disclosure will appreciate that a pharmaceutical composition comprising any inhibitor of gastric secretion may be used in the antisecretory therapy methods of the invention. The inhibitor of gastric secretion may be any composition which is capable of reducing gastric secretion when administered to a human patient, whether or not the gastric-secretion-inhibiting properties of the composition are presently recognized. The pharmaceutical composition which is useful in the methods of the invention includes, but is not limited to, any presently known inhibitors of gastric secretion, such as an histamine-$H_2$-receptor antagonist or a proton pump inhibitor.

Known pharmaceutical compositions which are useful in the methods of the invention thus include, but are not limited to, nizatidine (Axid®, Eli Lilly and Company, Indianapolis, Ind.), famotidine (Pepcid®, Merck & Co., West Point, Pa.), cimetidine (Tagamet®, SmithKline Beecham Pharmaceuticals, Philadelphia, Pa.), ranitidine (Zantac®, Glaxo Wellcome Inc., Research Triangle, N.C.), lansoprazole (Prevacid®, TAP Pharmaceuticals Inc., Deerfield, Ill.), omeprazole (Prilosec®, Astra Merck Inc., Wayne, Pa.), and other proton pump inhibitors which may become available. Dosing information for each of these known pharmaceutical compositions is described, for example, in Physician's Desk Reference ® (Medical Economics Co., Inc., Montvale, N.J., 51 st ed., 1997). Dosing information for using each of these known pharmaceutical compositions in the methods of the invention are the same as the dosing information for the use of each of these known pharmaceutical compositions for inhibiting gastric secretion, for example in the treatment of GERD. Methods of adapting the dosing information to individual human patients are within the ordinary level of skill in the art.

The invention encompasses the use of pharmaceutical compositions to practice the methods of the invention, the compositions comprising an inhibitor of gastric secretion and a pharmaceutically acceptable carrier.

As used herein, the term "lower GI disorder" means a disease of the lower gastrointestinal tract, including the small and large intestines and the rectum, and/or symptoms usually attributed to a dysfunction of one or more of these organs, such as diarrhea or lower abdominal cramps. A subset of lower GI disorders are those in which diarrhea is accompanied by postprandial urgency or a postprandial accentuation of the diarrhea. Lower GI disorders include those in which abdominal cramping or pain is an additional symptom. It is understood that lower GI disorders include both disorders for which an organic cause (e.g. infection by a parasite) is known and disorders for which no organic cause can be ascertained, such as IBS or FD. Lower GI disorders therefore include, but are not limited to, irritable bowel syndrome, functional diarrhea, ulcerative colitis, collagenous colitis, microscopic colitis, lymphocytic colitis, inflammatory bowel disease, Crohn's disease, and infectious diarrhea such as diarrhea associated with amebiasis, giardiasis, a viral infection, cytomegalovirus infection, or a pathogenic bacterial infection. The bacterial infection may, for example, be an infection by a bacterium selected from the group consisting of a bacterium of the genus Escherichia, an *Escherichia coli* 0157:H7 bacterium, a bacterium of the genus Salmonella, a bacterium of the genus Shigella, a bacterium of the genus Campylobacter, a bacterium of the species *Campylobacter jejuni*, and a bacterium of the genus Yersinia.

As used herein, the term "lower GI symptom" means a symptom associated with a lower GI disorder. Lower GI symptoms include, but are not limited to, diarrhea, chronic diarrhea, lower abdominal pain (meaning pain generally perceived below the umbilicus in a human), postprandial urgency, postprandial accentuation of diarrhea, and postprandial accentuation of lower abdominal pain.

As used herein, the term "acute diarrhea" means a diarrhea which is manifested in a human patient for a period of six weeks or less.

As used herein, the term "chronic diarrhea" means a diarrhea which is manifested in a human patient for a period of more than six weeks.

As used herein, the term "postprandial" refers to a symptom which seems, to a patient experiencing the symptom, to be exacerbated after the patient eats.

As used herein, the term "postprandial urgency" means an increase in the need perceived by a patient to move his or her bowels after the patient eats.

As used herein, the term "antisecretory therapy" means administration to a patient of a composition comprising an inhibitor of gastric secretion and a pharmaceutically acceptable carrier.

As used herein, an "effective amount" of an inhibitor of gastric secretion is an amount which, when administered to a human, causes a significant decrease in the amount of gastric juice and acid which is secreted by the human, the significant decrease being a decrease of at least 10%, and preferably 25%, 50%, 75%, or more than 75%.

As used herein, the term "pharmaceutically acceptable carrier" means a chemical composition with which an inhibitor of gastric secretion may be combined and which, following the combination, can be used to administer an inhibitor of gastric secretion to a human.

The pharmaceutical compositions useful for practicing the invention may be administered to deliver a dose of an inhibitor of gastric secretion of between 1 ng/kg/day and 100 mg/kg/day. In one embodiment, the invention envisions administration of a dose which results in a gastroenteric or systemic concentration of the inhibitor of gastric secretion between 1 nM and 1 M.

Pharmaceutical compositions that are useful in the methods of the invention may be administered in oral solid or liquid dosage forms, parentally, or in suppository, aerosol, topical or other similar dosage forms. In addition to an inhibitor of gastric secretion, such pharmaceutical compositions may contain pharmaceutically acceptable carriers and other ingredients known to enhance and facilitate drug administration. Other possible dosage forms, such as nanoparticles, liposomes, resealed erythrocytes, and immunologically based systems may also be used to administer an inhibitor of gastric secretion according to the methods of the invention.

For the sake of convenience, an inhibitor of gastric secretion may be packaged in a unit dosage form. A unit dosage form is a package, such as a pill, capsule, ampule, or suppository, for example, which comprises an entire dose or a portion of an entire dose which can be administered to a patient. For example, a unit dosage form may comprise an entire dose, whereby the patient is administered a single unit dosage form, or half of an entire dose, whereby the patient is administered two single unit dosage forms, and so on. By way of example, a unit dosage form comprising an entire dose of an inhibitor of gastric secretion which is useful in the antisecretory methods described herein may comprise about 30 milligrams of lansoprazole, about 20 milligrams of omeprazole, about 20 milligrams of famotidine, or about 150 milligrams of ranitidine.

As used herein, "alleviating a lower GI symptom" means reducing the severity or the frequency of the symptom or both.

As used herein, "alleviating a lower GI disorder" and "treating a patient afflicted with a lower GI disorder" are used interchangeably and mean reducing the frequency with which a symptom of the lower GI disorder is experienced by a patient, reducing the severity of the symptom, or both.

The efficacy of the pharmaceutical compositions useful in the methods of the invention may be improved by including a symptomatic anti-diarrheal agent therein. The use of symptomatic anti-diarrheal agents is well known in the art. Any symptomatic anti-diarrheal agent may be included in the pharmaceutical composition of the invention, whether or not the symptomatic anti-diarrheal properties of the agent are presently known. The pharmaceutical composition of the invention may include a presently-known symptomatic anti-diarrheal agent including, but not limited to hyoscyamine and atropine (e.g. Arco-Lase Plus ®, Arco Pharmaceuticals, Inc., Bohemia, N.Y.), furazolidone (e.g. Furoxone®, Roberts Pharmaceutical Corp., Eatontown, N.J.), loperamide (e.g. Imodium®A-D, McNeil Consumer Products Co., Fort Washington, Pa.), diphenoxylate (e.g. Lomotil®, G.D. Searle & Co., Chicago, Ill.), difenoxin (e.g. Motofen®, Carmick Laboratories, Inc., Cedar Knolls, N.J.), bismuth subsalicylate (e.g. Pepto-Bismol®, Proctor & Gamble, Cincinnati, Ohio), and octreotide (e.g. Sandostatin®, Sandoz Pharmaceuticals Corp., East Hanover, N.J.).

While not wishing to be bound by any particular theory, it is believed that gastric secretion affects postprandial intestinal motility by affecting acid-sensitive or volume-sensitive neural mediators, endocrine mediators, or both. Patients afflicted with IBS or FD who experience chronic diarrhea with postprandial urgency or accentuation of symptoms have been thought to have an exaggerated gastrocolic or gastroenteric response, at least with respect to moving lumenal contents distally. Paradoxically, IBS- or FD-afflicted patients who experience chronic diarrhea may have decreased postprandial motor responses, at least in the more distal colon, and these decreased responses may permit more rapid movement of colonic contents from the proximal to distal colon and less fluid absorption during such movement (Drossman et al., 1997, supra; Hasler et al., 1995; Lippincott Co., supra; Camilleri et al., supra;—O'Brien et al., supra; Bazzocchi et al., supra; Choi et al., supra; Johnson L. R., supra). Response of these patients to administration of inhibitors of gastric secretion, as described herein, suggests that the observed enhanced gastrocolic or gastroenteric response is mediated by acid-sensitive or volume-sensitive neural mediators, endocrine mediators, or both. Such mediators are most likely located in the proximal small intestine, but may also, or instead, be located in the stomach. These neural or endocrine mediators may be excessively responsive to normal amounts of acid, to normal volumes of gastric juice, or both, in FD- or IBS-afflicted patients. Alternately, or in addition, one or more organs responsible for abnormal motility may be excessively responsive to normal amounts of mediator stimulation in such patients. According to either model, reduction of gastric secretion would be expected to affect one or more organs responsible for abnormal motility.

Acid in the duodenum and stomach has many known endocrine, paracine, neural, and resultant physiological effects including, but not limited to, effects upon secretion of somatostatin, gastrin, secretin, pancreatic juice, and bile, and effects upon the rate of gastric emptying (Johnson, L.R. supra). Whether any of the known effects of gastric acid secretion are involved in the gastrocolic response is unclear. Secretin, for example, probably inhibits motor activity in the sigmoid colon. While not wishing to be bound by any particular theory, it is possible that secretin is the acid-sensitive mediator responsible for the apparent decreased postprandial motor activity observed in the distal colon of FD- and IBS-afflicted patients.

Inhibitors of gastric secretion reduce the volume of gastric juice secreted in patients to whom such inhibitors are administered. While again not wishing to be bound by any particular theory, it is possible that the reduced volume of gastric secretion, rather than, or in addition to, the reduced acid secretion, is responsible for thie beneficial effects of the inhibitors of gastric secretion described herein. Reduced gastric volume reduces gastric distention and may therefore be expected to reduce the gastrocolic response and the rate of gastric emptying, which is thought by some investigators to be abnormally increased in at least some FD- and IBS-afflicted patients (Wiley et al., supra; Phillips et al., 1997, Mayo Clin. Proc. 72:434–438).

While still not wishing to be bound by any particular theory, it is likely that the compounds described herein function by reducing the common gastrocolic response to eating. This fact, in combination with the present disclosure, suggests that the methods of the invention are also applicable to alleviation of organic lower GI disorders which are associated with a lower GI symptom such as diarrhea, postprandial urgency, and cramps. Such disorders include, but are not limited to, Crohn's disease, infectious diarrheas, ulcerative colitis, microcytic colitis, and the like.

The invention includes a kit for alleviating a lower GI symptom such as diarrhea, postprandial urgency, or cramps in a human patient afflicted with a lower GI disorder, the kit comprising an inhibitor of gastric secretion and an instruction for administering the inhibitor according to the methods of the invention. The instruction may, for example, be affixed to a container which contains the inhibitor or be shipped together with a container which contains the inhibitor. Alternatively, the instruction may be shipped separately from the container with the intention that the instruction and the inhibitor be used together by the recipient.

The invention also includes a kit for alleviation of a lower GI disorder in a human patient, the kit comprising an inhibitor of gastric secretion and an instructional material which describes administering the inhibitor according to the methods of the invention. The instructional material may, for example, be affixed to a container which contains the inhibitor or be shipped together with a container which contains the inhibitor. Alternatively, the instructional material may be shipped separately from the container with the intention that the instructional material and the inhibitor be used together by the recipient.

As used herein, an "instructional material" includes a publication, a recording, a diagram, or any other medium of expression which can be used to communicate the usefulness of the composition of the invention for alleviating a lower GI symptom of a lower GI disorder or for alleviating a lower GI disorder in a human.

The instructional material for either kit of the invention may, for example, comprise inhibitor dosing information specifically developed for an individual patient afflicted with a lower GI disorder, generalized inhibitor dosing information for patients afflicted with a lower GI disorder, a description of the inhibitor of the type found in standard references such as Physicians' Desk Reference ® (Medical Economics Co., Inc., Montvale, N.J., 51st ed., 1997) wherein the utility of the inhibitor for alleviating a lower GI disorder or alleviating a symptom thereof is described, an article or a copy thereof obtained from a medical or scientific journal wherein the utility of the inhibitor for alleviating a lower GI disorder or alleviating a symptom thereof is described, a patent or patent application or a copy thereof wherein the utility of the inhibitor for alleviating a lower GI disorder or alleviating a symptom thereof is described, or the like.

The invention is now described with reference to the following Examples. These Examples are provided for the purpose of illustration only, and the invention should in no way be construed as being limited to these Examples, but rather should be construed to encompass any and all variations which become evident as a result of the teaching provided herein.

EXAMPLE 1

Two Studies

Five patients, each of whom exhibited symptoms of both GERD and IBS or FD were orally administered 30 milligrams per day of lansoprazole (Prevacid®, TAP Pharmaceuticals Inc., Deerfield, Ill.), an inhibitor of gastric secretion, with the intention of merely relieving the heartburn symptoms associated with GERD. Each of the five patients experienced relief of the heartburn symptoms associated with GERD following administration of this compound. The use of an inhibitor of gastric secretion to alleviate heartburn associated with GERD is known in the art. Unexpectedly, however, each of these five patients also experienced rapid relief of the chronic diarrhea and postprandial urgency symptoms associated with IBS or FD. To determine if this surprising result was merely fortuitous, a prospective therapeutic study was conducted involving twenty patients, each of whom was afflicted with IBS or FD and experienced chronic diarrhea with postprandial urgency or accentuation of symptoms. None of the five GERD-afflicted patients was included in the prospective therapeutic trial of the twenty IBS- or FD-afflicted patients.

Each of the twenty patients in the prospective therapeutic trial, sixteen of whom were female, had experienced persistent or intermittent watery or loose stools. They experienced between four and fifteen bowel movements per day, which were sometimes accompanied by passage of mucus, and had a median value of six bowel movements per day, for a period beginning as recently as three months and as long as twenty years prior to the beginning of the prospective therapeutic trial. The median duration of pre-trial persistent or intermittent watery or loose stool experience was about one year. All twenty of the patients also experienced postprandial urgency or accentuation of symptoms, which they sometimes attributed to specific foods other than lactose. The onset of chronic diarrhea in the twenty patients usually began in the second to fourth decade of life, with the median age of onset being thirty-four years.

A minority of the twenty patients could sometimes associate exacerbation of symptoms with emotional stress. Some of the twenty patients experienced abdominal discomfort associated with their chronic diarrhea symptoms and thus would be labeled as IBS patients, although pain was not a prominent symptom in most of the twenty patients. Each of the twenty patients generally looked well and did not have constitutional or "alarming" symptoms or findings, such as fever, anorexia, significant weight loss, unexplained anemia, or any significant abnormal physical findings. Diagnostic tests designed to detect known organic causes of chronic diarrhea were negative for the patients. These diagnostic tests included examination and culture of stool for pathogens, including parasites, detection of stool fat or hemoccult blood, colonoscopy with multiple biopsies, upper endoscopy, small bowel x-ray imaging, trial of a lactose-free diet, routine blood and urine tests, and tests for endocrine abnormalities, such as thyroid tests, 5-OH-indole acetic acid, and serum gastrin.

The twenty patients had received only limited relief from previous conventional IBS therapies, such as maintenance of a restrictive diet or administration of fiber, loperamide, diphenoxylate, other opiates, anticholinergics, or sedatives.

Each of the twenty IBS- or FD-afflicted patients was referred to a gastroenterologist by a primary care physician and was orally administered an inhibitor of gastric acid secretion. Thirteen of the twenty patients were administered 30 milligrams per day of lansoprazole (Prevacid®, TAP Pharmaceuticals Inc., Deerfield Ill.). One of the twenty patients was administered 20 milligrams per day of omeprazole (Prilosec®, Astra Merck Inc., Wayne, Pa.). Three of the twenty patients were administered 20 milligrams of famotidine (Pepcid®, Merck & Co., West Point, Pa.) twice per day. The remaining three of the twenty patients were administered 150 milligrams of ranitidine (Zantac®, Glaxo Wellcome Inc., Research Triangle, N.C.) twice per day.

Each of the five GERD-afflicted patients and each of the twenty IBS- or FD-afflicted patients involved in the prospective therapeutic trial experienced rapid, substantial alleviation of their chronic diarrhea and postprandial urgency symptoms, usually within three days following the onset of administration of the gastric secretion inhibitor. During treatment, each of the twenty patients involved in the prospective therapeutic trial produced between about one and three formed stools per day. Furthermore, the abdominal discomfort associated with the chronic diarrhea symptoms of those patients who experienced such discomfort was relieved. Improvement continued during the one- to four-month period that each of the twenty patients in the prospective trial was treated and observed.

One patient who became constipated while taking lansoprazole (Prevacid®, TAP Pharmaceuticals Inc., Deerfield, Ill.), became more regular when switched to famotidine (Pepcid®, Merck & Co., West Point, Pa.).

The number of daily bowel movements of one of the twenty patients was reduced from an average of fifteen movements to between three and five movements following administration of ranitidine (Zantac®, Glaxo Wellcome Inc., Research Triangle, N.C.). This patient's number of daily bowel movements was further reduced to between two and three after the patient was switched to lansoprazole (Prevacid®, TAP Pharmaceuticals Inc., Deerfield, Ill.).

Five of the twenty patients stopped antisecretory therapy, but experienced recurrent diarrhea within a few days following cessation of therapy. However, each of these five patients experienced relief from diarrhea within a few days following resumption of antisecretory therapy.

Three of the twenty patients who had histories of chronic intermittent diarrhea remained free from diarrhea for up to one month after stopping antisecretory therapy. One of these three patients replaced her antisecretory therapy with a less expensive anti-diarrheal agent. Another of these three patients obtained a new, less stressful job.

In summary, all five of the GERD-afflicted patients who were afflicted with IBS or FD and all twenty of the IBS- or FD-afflicted patients involved in the prospective therapeutic trial experienced dramatic and rapid relief from their chronic diarrhea and postprandial urgency symptoms following administration of an inhibitor of gastric secretion. All of those patients who experienced abdominal discomfort associated with chronic diarrhea also experienced relief from that discomfort following administration of an inhibitor of gastric secretion.

In the past, many patients afflicted with IBS responded to placebo therapies, especially during the short-term use of those placebo treatments (Drossman et al., 1997, Gastroenterology 112:2120–2137; Hasler et al., 1995, In: *Textbook of Gastroenterology*, 2nd ed., Yamada, Ed., J.B. Lippincott Co., Philadelphia, pp. 18321855; Camilleri et al., 1977, Aliment Pharmacol Ther. 11:3–15; Drossman et al., 1994, *The functional Gastrointestinal disorders: Diagnosis, Pathophysiology, and Treatment*, Degnon and Associates, McLean, Va.; Klein, 1988, Gastroenterology 95:232–241). Because the patients involved in the studies described herein were referred from primary care physicians to a gastroenterologist for timely diagnosis and effective therapy, rather than for study, it was ethically required that only drugs thought to be rapidly effective would be used for therapy. Therefore, no patients included in the studies described herein were administered placebo treatments. Nonetheless, the results of the studies described herein do not reflect a placebo effect.

The dramatic and rapid responses of all of the patients to the inhibitors of gastric secretion, which responses permitted ethical continued use of the inhibitors, were unlikely merely placebo effects because all twenty-five patients responded significantly and rapidly. Furthermore, the therapeutic effectiveness continued for the duration of therapy, up to four months, the maximum period of study. In addition, there were no expectations, either on the part of the initial five patients afflicted with GERD or on the part of the investigators treating those five patients, that an inhibitor of gastric secretion would provide relief from the five patients' chronic diarrhea and postprandial symptoms.

A placebo effect was similarly unlikely among the twenty prospective patients afflicted with IBS or FD, because such remarkable relief from chronic diarrhea symptoms had not been experienced previously when conventional IBS therapies had been used by these twenty patients or by the investigators when treating similar patients. Five patients stopped therapy, and experienced a recurrence of their chronic diarrhea symptoms within a few days. Each of these five patients who stopped therapy experienced relief within a few days following resumption of antisecretory therapy.

The patients described in these studies, who were successfully treated using antisecretory agents, were all afflicted with IBS or FD and experienced postprandial urgency or accentuation of symptoms. The precise underlying abnormalities in each of these patients, and the exact mechanism responsible for their therapeutic responses were not determined. However, by reducing the secretion of gastric acid, the volume of gastric juice, or both, the antisecretory therapy described herein probably diminished an exaggerated acid-sensitive or volume-sensitive gastrocolic or gastroenteric response to eating. By suppressing this response, antisecretory drugs are also effective for treatment of patients afflicted with lower GI symptoms associated with organic lower GI disorders, especially those disorders in which the patient's lower GI symptoms are made worse by eating.

EXAMPLE 2

Additional Studies

The studies described in this Example confirm that antisecretory therapy, as described herein, relieves lower GI symptoms, and particularly postprandial lower GI symptoms. These studies demonstrate that inhibition of gastric secretion relieves postprandial urgency, diarrhea, and cramps, not only in patients afflicted with IBS or FD, but also in patients afflicted with organic lower GI disorders. Inhibition of gastric secretion may both alleviate lower GI symptoms and permit better eating and nutrition in patients afflicted with IBS, FD, and organic lower GI disorders. While not wishing to be bound by any particular theory, it is believed that antisecretory therapy alleviates lower GI symptoms by diminishing the gastrocolic reflex, the gastroenteric reflex, or both.

In the studies described in this Example, 30 milligrams of lansoprazole per day were administered to individual patients who were afflicted with chronic diarrhea and who either did or did not experience postprandial urgency or postprandial accentuation of symptoms. None of the patients described in this Example are patients described in Example 1.

The following eighteen patients who experienced chronic diarrhea and postprandial urgency responded to lansoprazole administration, usually within three days: 1) a 37-year-old male patient who was subsequently determined to be afflicted with ulcerative colitis; 2) and 3) a 58-year-old male patient and a 71-year-old female patient, each of whom was subsequently determined to be afflicted with collagenous colitis; 4) a 27-year-old female patient who was subsequently determined to be afflicted with giardiasis; and 5)–18) fourteen patients afflicted with IBS or FD. Each of these eighteen patients experienced relief of postprandial urgency and cramps (if present), and usually attained from one to three formed bowel movements (BMs) per day. Patients in the studies described in this Example were administered lansoprazole before specific diagnoses were made and before specific therapy was started for any subsequently diagnosed organic condition.

Two patients who experienced chronic diarrhea and postprandial urgency failed to respond to administration of lansoprazole. One of these two patients was later determined to be afflicted with lactase deficiency which was responsive to a lactose-free diet. The other of these two patients was known to be afflicted with severe Crohn's colitis and had been poorly responsive to treatment with the steroids, 6-mercaptopurine and 5-amino salicylic acid.

A 75-year-old male patient who had been afflicted with acute diarrhea for nine days and who did not respond to administration of loperamide experienced marked relief of his postprandial urgency and modest reduction in diarrhea within three days following administration of lansoprazole. This patient experienced complete relief when infection of the patient by *E. coli* 0157:H7 was subsequently diagnosed and treated.

Four patients who were afflicted with chronic diarrhea but did not experience postprandial urgency did not respond to administration of lansoprazole. These four included two patients afflicted with collagenous colitis, one patient afflicted with ulcerative colitis, and a patient afflicted with cholereic diarrhea following performance of an ileal resection on that patient.

One patient afflicted with chronic diarrhea who did not experience postprandial urgency and who was subsequently found to be afflicted with ulcerative colitis experienced an improvement in diarrhea following administration of lansoprazole. This patient produced about six watery BMs per day prior to lansoprazole administration and two or three soft BMs per day following lansoprazole administration.

The studies described in this Example demonstrate that antisecretory therapy, as described herein, alleviates lower GI symptoms, and particularly postprandial lower GI symptoms, in patients afflicted with a variety of lower GI disorders. Symptoms which were alleviated included diarrhea, chronic diarrhea, pain, and postprandial symptoms such as postprandial urgency. Antisecretory therapy was effective for alleviation of organic lower GI disorders including ulcerative colitis, collagenous colitis, giardiasis, and bacterial infection by E. coli 0157:H7. Antisecretory was also effective for alleviation of IBS and FD.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of alleviating a lower gastrointestinal (GI) disorder in a human patient, the method comprising administering to the patient a pharmaceutical composition comprising an effective amount of an inhibitor of gastric secretion, wherein the lower GI disorder is not selected from the group consisting of collagenous colitis, ulcerative colitis, and Crohn's disease.

2. The method of claim 1, wherein the lower GI disorder is not attributable to an organic cause.

3. The method of claim 2, wherein the lower GI disorder is selected from the group consisting of irritable bowel syndrome and functional diarrhea.

4. The method of claim 1, wherein the lower GI disorder is selected from the group consisting of irritable bowel syndrome, functional diarrhea, microscopic colitis, lymphocytic colitis, infectious diarrhea, lactase deficiency, infectious diarrhea, amebiasis, giardiasis, a viral infection, cytomegalovirus infection, a pathogenic bacterial infection, an infection by a bacterium of the genus Escherichia, an Escherichia coli 0157:H7 infection, an infection by a bacterium of the genus Salmonella, an infection by a bacterium of the genus Shigella, an infection by a bacterium of the genus Campylobacter, and an infection by a bacterium of the genus Yersinia.

5. The method of claim 1, wherein the lower GI disorder is characterized by a lower GI symptom selected from the group consisting of diarrhea, chronic diarrhea, acute diarrhea, abdominal pain associated with diarrhea, postprandial urgency, postprandial accentuation of diarrhea, postprandial accentuation of abdominal pain, and a combination of these symptoms.

6. The method of claim 5, wherein the lower GI disorder is characterized by diarrhea and a postprandial symptom selected from the group consisting of postprandial urgency and postprandial accentuation of diarrhea.

7. The method of claim 1, wherein the inhibitor of gastric secretion is selected from the group consisting of a proton pump inhibitor, a histamine $H_2$-receptor blocker, omeprazole, lansoprazole, cimetidine, ranitidine, nizatidine, and famotidine.

8. The method of claim 1, wherein gastric secretion is suppressed by administering about 30 milligrams of lansoprazole per day to the patient.

9. The method of claim 1, wherein gastric secretion is suppressed by administering about 20 milligrams of omeprazole per day to the patient.

10. The method of claim 1, wherein gastric secretion is suppressed by administering about 20 milligrams of famotidine twice per day to the patient.

11. The method of claim 1, wherein gastric secretion is suppressed by administering about 150 milligrams of ranitidine twice per day to the patient.

12. The method of claim 1, wherein the pharmaceutical composition further comprises a symptomatic anti-diarrheal agent.

13. The method of claim 12, wherein the agent is selected from the group consisting of loperamide, hyoscyamine, atropine, furazolidone, loperamide, diphenoxylate, difenoxin, bismuth subsalicylate, and octreotide.

14. A method of alleviating a lower GI symptom in a patient afflicted with a lower GI disorder, the method comprising administering to the patient a pharmaceutical composition comprising an effective amount of an inhibitor of gastric secretion.

15. A method of alleviating a lower GI disorder in a human patient, the method comprising administering an inhibitor of gastric secretion other than omeprazole to the patient.

16. The method of claim 15, wherein the lower GI disorder is not attributable to an organic cause.

17. The method of claim 15, wherein the lower GI disorder is selected from the group consisting of irritable bowel syndrome, fluctional diarrhea, ulcerative colitis, collagenous colitis, microscopic colitis, lymphocytic colitis, inflammatory bowel disease, Crohn's disease, infectious diarrhea, ulcerative bowel disease, lactase deficiency, infectious diarrhea, amebiasis, giardiasis, a viral infection, cytomegalovirus infection, a pathogenic bacterial infection, an infection by a bacterium of the genus Escherichia, an Escherichia coli 0157:H7 infection, an infection by a bacterium of the genus Salmonella, an infection by a bacterium of the genus Shigella, an infection by a bacterium of the genus Campylobacter, and an infection by a bacterium of the genus Yersinia.

18. The method of claim 15, wherein the inhibitor of gastric secretion is selected from the group consisting of a proton pump inhibitor other than omeprazole, a histamine $H_2$-receptor blocker, lansoprazole, cimetidine, ranitidine, nizatidine, and famotidin.

19. A method of alleviating a lower GI disorder in a human patient, the method comprising administering an inhibitor of gastric secretion to the patient, wherein if the lower GI disorder is selected from the group consisting of collagenous colitis, ulcerative colitis, and Crohn's disease, then the inhibitor is not omeprazole.

* * * * *